US008652337B1

(12) United States Patent
Afzali-Ardakani et al.

(10) Patent No.: US 8,652,337 B1
(45) Date of Patent: Feb. 18, 2014

(54) SELF-FORMED NANOMETER CHANNEL AT WAFER SCALE

(71) Applicant: International Business Machines Corporation, Armonk, NY (US)

(72) Inventors: Ali Afzali-Ardakani, Ossining, NY (US); Binquan Luan, Pleasantville, NY (US); Gustavo A. Stolovitzky, Riverdale, NY (US); Chao Wang, Ossining, NY (US); Deqiang Wang, Ossining, NY (US)

(73) Assignee: International Business Machines Corporation, Armonk, NY (US)

( * ) Notice: Subject to any disclaimer, the term of this patent is extended or adjusted under 35 U.S.C. 154(b) by 0 days.

(21) Appl. No.: 13/971,468

(22) Filed: Aug. 20, 2013

Related U.S. Application Data

(63) Continuation of application No. 13/738,298, filed on Jan. 10, 2013.

(51) Int. Cl.
*H01B 13/00* (2006.01)

(52) U.S. Cl.
USPC .............................. 216/17; 438/700; 977/742

(58) Field of Classification Search
USPC ................................ 216/13; 213/17; 977/742
See application file for complete search history.

(56) References Cited

U.S. PATENT DOCUMENTS 7,211,143 B2 * 5/2007 Yang et al ..................... 117/84
7,276,389 B2 * 10/2007 Kim et al. ........................ 438/34
8,093,628 B2 * 1/2012 Yang et al. ..................... 257/200
2011/0034008 A1 * 2/2011 Kianian ......................... 438/478

OTHER PUBLICATIONS

Cao et al., "Fabrication of 10 nm Enclosed Nanofluidic Channels," Applied Physics Letters; vol. 81, No. 1, Jul. 1, 2002; 3 pages.*
Choi et al., "Fabrication of 20 nm Embedded Longitudinal Nanochannels Transferred from Metal Nanowire Patterns," Fabrication Technology; IEEE 16th International MEMS Conference, Kyoto, Japan, Feb. 20, 2003, 2 pages.*
Han et al., "Entropic Trapping and Escape of Long DNA Molecules at Submicron Size Constriction," Physical Review Letters; vol. 83, No. 8; Aug. 23, 1999; 4 pages.*
Hoang et al., "Fabrication and Interfacing of Nanochannel Devices for Single-Molecule Studies," IOP Publishing, Journal of Micromechanics and Microengineering; J. Micromech. Microeng. 19 (2009) 065017 (10pp); 11 pages.*

(Continued)

*Primary Examiner* — Roberts Culbert
(74) *Attorney, Agent, or Firm* — Cantor Colburn LLP; Vazken Alexanian (57) ABSTRACT

A mechanism is provided for fabricating nanochannels for a nanodevice. Insulating film is deposited on a substrate. A nanowire is patterned on the film. Insulating material is deposited on the nanowire and film. A first circular hole is formed in the insulating material as an inlet, over a first tip of the nanowire to expose the first tip. A second circular hole is formed as an outlet, over a second tip of the nanowire opposite the first tip to expose the second tip. A nanochannel connects the first and second holes by etching away the nanowire via an etchant in the first and the second holes. A first reservoir is attached over the first hole in connection with the nanochannel at a previous location of the first tip. A second reservoir is attached over the second hole in connection with the nanochannel at a previous location of the second tip.

20 Claims, 12 Drawing Sheets

(56) References Cited

OTHER PUBLICATIONS

Holt et al., "Fast Mass Transport Through Sub-2-Nanometer Carbon Nanotubes," Science AAAS, 312, 1034 (2006); DOI: 10.1126/science.1126298; 5 pages.*

Ivanov et al., "DNA Tunneling Detector Embedded in a Nanopore," Nano Lett. 2011, 11,279-285; Received for review: Nov. 3, 2010; published on web: Dec. 6, 2010; 7 pages.*

Letant et al., "Nanochannel Arrays on Silicon Platforms by Electrochemistry," Nano Letters, 2004, vol. 4, No. 9, 1705-1707, 3 pages.*

Liang et al., "Nanogap Detector Inside Nanofluidic Channel for Fast Real-Time Label-Free DNA Analysis," Nano Letters, 2008 vol. 8, No. 5, 1472-1476; 5 pages.*

O'Brien et al., "Fabrication of an Integrated Nanofluidic Chip Using Interferometric Lithography," 2003 American Vacuum Society; J. Vac. Sci. Technol. B 21(6), Nov./Dec. 2003; 5 pages.*

Perry et al., "Review of Fabrication of Nanochannels for Single Phase Liquid Flow," Microfluid Nanofluid (2006) 2: 185-193; 9 pages.*

Riehn et al., "Restriction Mapping in Nanofluidic Devices," PNAS; Departments of Physics and Molecular Biology, Princeton University; May 12, 2005; www.pnas.org/cgi/doi/10.1073/pnas.0503809102; 5 pages.*

Stein et al., "Suface-Charge-Governed Ion Transport in Nanofluidic Channels," Physical Review Letters; vol. 93, No. 3, week ending Jul. 16, 2004; 4 pages.*

Stewart et al, "DNA-Templated Nanowires as Sacrificial Materials for Creating Nanocapillaries," Proc. of SPIE, vol. 7035, 2008, 70350H, 8 pages.*

Turner et al., "Monolithic Nanofluid Sieving Structures for DNA Manipulation," Journal of Vacuum Science and Technology; http://dx.doi.org/10.1116/1.590419; 1998; 7 pages.*

Ivanov et al., "DNA Tunneling Detector Embedded in a Nanopore," Nano Lett. 2011, 11, 279-285; Received for review: Nov. 3, 2010; published on web: Dec. 6, 2010; 7 pages.

Letant et al., "Nanochannel Arrays on Silicon Platforms by Electrochemistry," Nano Letters, 2004, vol. 4, No. 9, 1705-1707, Received Jun. 9, 2004; 3 pages.

Perry et al., "Review of Fabrication of Nanochannels for Single Phase Liquid Flow," Microfluid Nanofluid (2006) 2: 185-193; Received Aug. 2005; 9 pages.

Turner et al., "Monolithic Nanofluid Sieving Structures for DNA Manipulation," Journal of Vacuum Science and Technology; http://dx.doi.org/10.1116/1.590419; 1998; 7 pages.

* cited by examiner

SELF-FORMED NANOMETER CHANNEL AT WAFER SCALE

CROSS REFERENCE TO RELATED APPLICATIONS

The present application is a continuation of U.S. patent application Ser. No. 13/738,298, entitled "SELF-FORMED NANOMETER CHANNEL AT WAFER SCALE", filed on Jan. 10, 2013, which is incorporated herein by reference in its entirety.

BACKGROUND

The present invention relates to nanochannels, and more specifically, to self-formed nanochannels for nanodevices.

Nanopore sequencing is a method for determining the order in which nucleotides occur on a strand of deoxyribonucleic acid (DNA). A nanopore (also referred to a pore, nanochannel, hole, etc.) can be a small hole in the order of several nanometers in internal diameter. The theory behind nanopore sequencing is about what occurs when the nanopore is submerged in a conducting fluid and an electric potential (voltage) is applied across the nanopore. Under these conditions, a slight electric current due to conduction of ions through the nanopore can be measured, and the amount of current is very sensitive to the size and shape of the nanopore. If single bases or strands of DNA pass (or part of the DNA molecule passes) through the nanopore, this can create a change in the magnitude of the current through the nanopore. Other electrical or optical sensors can also be positioned around the nanopore so that DNA bases can be differentiated while the DNA passes through the nanopore.

The DNA can be driven through the nanopore by using various methods, so that the DNA might eventually pass through the nanopore. The scale of the nanopore can have the effect that the DNA may be forced through the hole as a long string, one base at a time, like thread through the eye of a needle. Recently, there has been growing interest in applying nanopores as sensors for rapid analysis of biomolecules such as deoxyribonucleic acid (DNA), ribonucleic acid (RNA), protein, etc. Special emphasis has been given to applications of nanopores for DNA sequencing, as this technology holds the promise to reduce the cost of sequencing below $1000/human genome.

SUMMARY

According to an embodiment, a method for fabricating nanochannels for a nanodevice is provided. The method includes depositing an electrically insulating film on a substrate, patterning a nanowire on the electrically insulating film, depositing an electrically insulating material on both the nanowire and the electrically insulating film, and forming a first circular hole in the electrically insulating material as an inlet. The first circular hole is formed over a first tip of the nanowire, and the first circular hole exposes the first tip. The method includes forming a second circular hole as an outlet. The second circular hole is formed over a second tip of the nanowire opposite the first tip, and the second circular hole exposes the second tip. Also, the method includes forming a nanochannel connecting the first circular hole to the second circular hole by etching away the nanowire via flowing an etchant in the first circular hole and out the second circular hole. The method includes attaching a first reservoir over the first circular hole to be in connection with the nanochannel at a previous location of the first tip, and attaching a second reservoir over the second circular hole to be in connection with the nanochannel at a previous location of the second tip.

According to an embodiment, a method for fabricating nanochannels for a nanodevice is provided. The method includes depositing an electrically insulating film on a substrate, patterning nanowires on the electrically insulating film, depositing an electrically insulating material on both the nanowires and the electrically insulating film, and forming first circular holes in the electrically insulating material as inlets. The first circular holes are respectively formed over first tips of the nanowires. The first circular holes respectively expose the first tips. The method includes forming second circular holes as outlets. The second circular holes are respectively formed over second tips of the nanowires opposite the first tips, and the second circular holes respectively expose the second tips. Also, the method includes forming the nanochannels respectively connecting the first circular holes to the second circular holes by etching away the nanowires via flowing an etchant in the first circular holes and out the second circular holes, attaching first reservoirs individually over the first circular holes to be in connection respectively with the nanochannels at previous locations of the first tips, and attaching second reservoirs individually over the second circular holes to be in connection respectively with the nanochannels at previous locations of the second tips.

Additional features and advantages are realized through the techniques of the present invention. Other embodiments and aspects of the invention are described in detail herein and are considered a part of the claimed invention. For a better understanding of the invention with the advantages and the features, refer to the description and to the drawings.

BRIEF DESCRIPTION OF THE SEVERAL VIEWS OF THE DRAWINGS

The subject matter which is regarded as the invention is particularly pointed out and distinctly claimed in the claims at the conclusion of the specification. The forgoing and other features, and advantages of the invention are apparent from the following detailed description taken in conjunction with the accompanying drawings in which:

FIGS. 1A through 1D illustrate processes to fabricate a nanometer channel (i.e., nanochannel) in a nanodevice according to an embodiment, in which:

FIGS. 2A through 2C illustrate processes to fabricate an array of nanometer channels (i.e., nanochannels) at the wafer scale in a nanodevice according to an embodiment, in which:

DETAILED DESCRIPTION

According to an embodiment, a method is provided to fabricate an array of nanometer channels (also referred to as nanochannels) at the wafer scale for DNA sequencing or other lab-on-a-chip-based analysis of biomolecules. A nanometer channel can provide a platform to study molecular behaviors at the single molecule scale. The micro/nano channel can sort, manipulate, and detect the DNA samples. There are many possible ways to fabricate nanochannels, which include optical lithography, electron beam lithography, focus ion beam, nanoimprint lithography, and interferometic lithography. Each method has its own advantages, but it is very difficult to fabricate sub-10-nanometer nanochannels by using those techniques.

In an embodiment, a method is introduced to fabricate (2D) nanochannels at sub-10 nanometers, close to the physical dimension of target molecules (such as DNA, RNA, and amino acids), so that the nanochannel can further confine the motion of a DNA/RNA molecule in lateral directions. This allows nanoscopic information to be studied about the molecular transport of the target molecule in nanofluidic channels. Also the method can be scaled up to make nanometer channels at the wafer level.

FIGS. 1A through 1D illustrate processes to fabricate a nanometer channel (i.e., nanochannel) in a nanodevice 100 (and a nanodevice 200) for DNA/RNA sequencing or peptide detection. FIGS. 1A through 1D show processes for one nanochannel but apply to numerous nano channels.

Figure 1A:
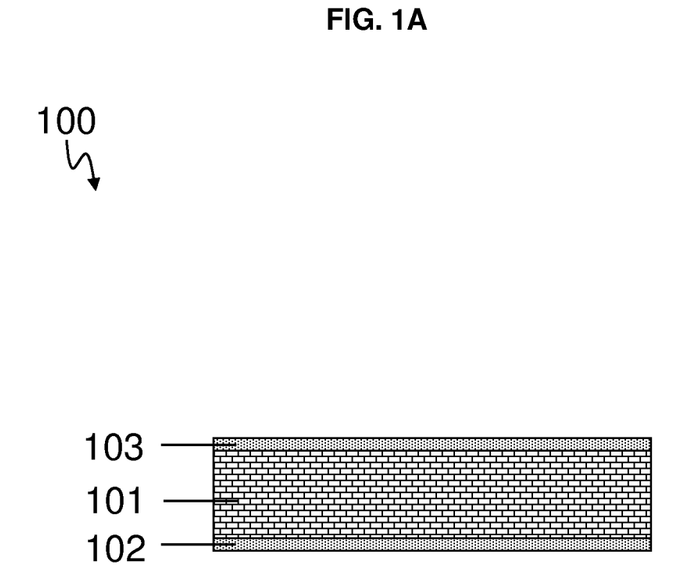
FIG. 1A illustrates an electrically insulating substrate with an electrically insulating thin film underneath and an electrically insulating thin film above.

FIG. 1A shows an electrically insulating substrate 101 which may include a material such as silicon. An electrically insulating thin film 102 may be deposited under the insulating substrate 101. An electrically insulating thin film 103 may be deposited on top of the insulating substrate 101.

The electrically insulating thin films 102 and 103 may include materials, such as hafnium oxide, silicon dioxide, etc. The electrically insulating substrate 101 may have a thickness of 700 micrometers for a 200 mm in diameter wafer, and the electrically insulating thin films 102 and 103 may have a thickness of several (e.g., 2, 3, 4, 5, etc.) or tens (10, 15, 20, 25, 30, etc.) of nanometers.

As discussed herein, view (A) is a cross-sectional view of the nanodevice 100 and 200, and view (B) is the top-view of the nanodevice 100 and 200.

Figure 1B:
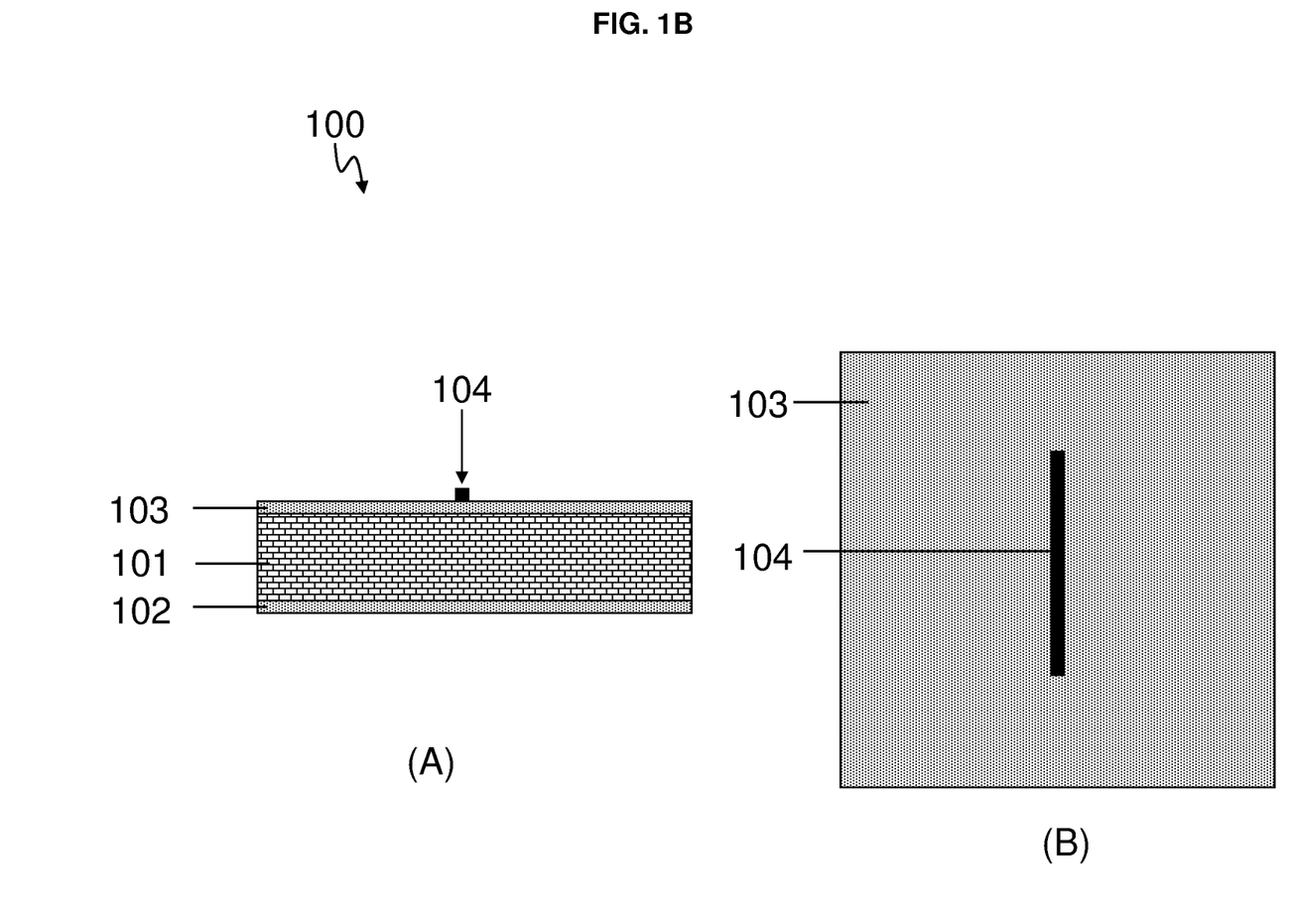
FIG. 1B illustrates a nanowire selectively positioned on the insulating thin film.

In FIG. 1B, a nanowire 104 (a nanometer wire) is selectively placed on the insulating thin film 103. The nanowire 104 may be a single-wall or multiwall carbon nanotube, silicon nanowire, etc.

Figure 1C:
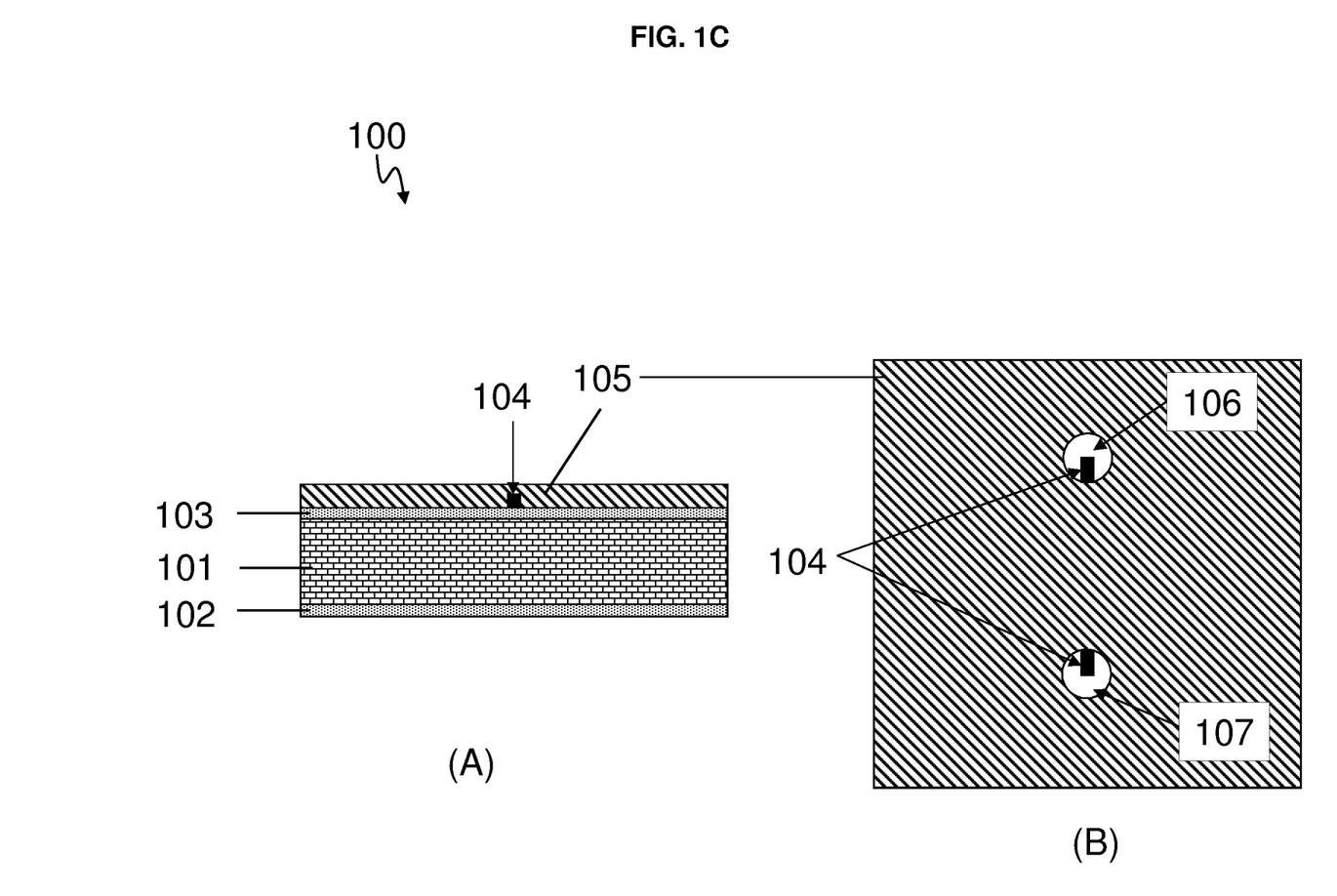
FIG. 1C illustrates an insulating material deposited on both the insulating thin film and the nanowire.

An insulating material 105 is deposited on both the insulating thin film 103 and the nanowire 104 as seen in FIG. 1C. The insulating material 105 may be any insulating material, such as silicon dioxide. The insulating material 105 may have a thickness of several times the diameter of nanowire, like tens (e.g., 10, 15, 20, 25, etc.) of nanometers.

The insulating material 105 covers the nanowire 104, and two openings 106 and 107 are opened for a nanochannel. The two openings 106 and 107 can be opened by reactive ion etching as understood by one skilled in the art. The two opening 106 and 107 may have a diameter of 100 micrometers (µm) to 1 millimeter (mm). In order to prevent shortage from the substrate 101, the depth of the two openings 106 and 107 is the thickness of nanowire 104. Particularly, the depth of the openings 106 and 107 will stop at the insulating thin film 103 (e.g., without penetrating or going through the insulating thin film 103).

Figure 1D:
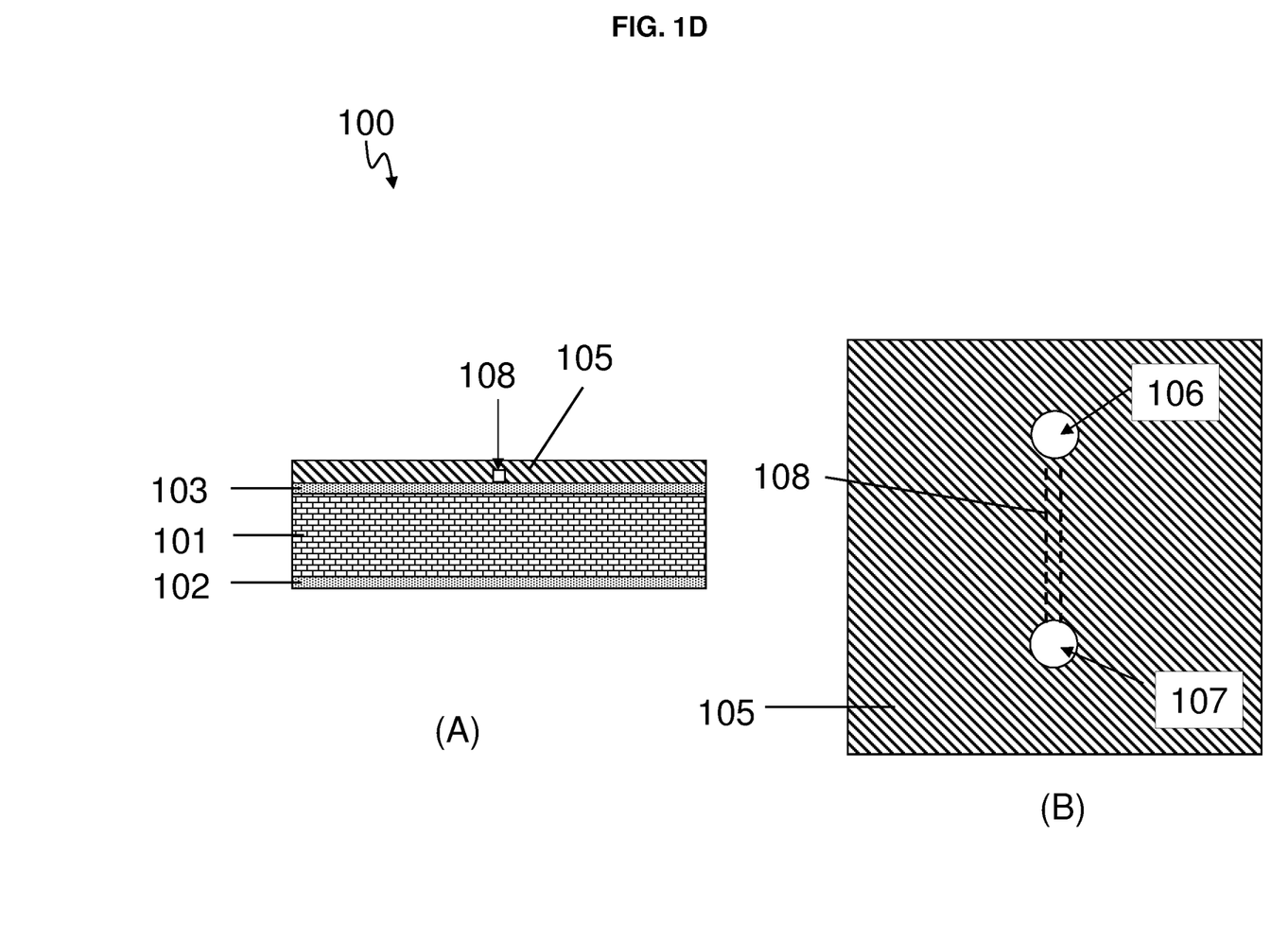
FIG. 1D illustrates the nanochannel formed by removing the nanowire which was previously covered by the insulating material.

In FIG. 1D, the nanochannel 108 (nanometer channel) is formed by removing the nanowire 104 which was covered by the insulating material 105. Oxygen plasma can be used to remove the nanowire 104 (e.g., carbon nanotube), thus leaving the patterned nanochannel 108 in place of the nanowire 104. The length of the nanochannel 108 can be from a few nanometers (e.g., 4 nanometers) to hundreds of micrometers. The gas (of the oxygen plasma) can easily pass through and etch away the carbon nanotube (i.e., nanowire 104) with a length of a few nanometers (e.g., 4 nanometers) to a few micrometers. The parameters (temperature, pressure) can be adjusted to control the etch rate for carbon nanotube to have a different length. The openings 106 and 107 are to be the inlet and the outlet of a fluidic nanochannel 108 (as understood by one skilled in the art). The diameter of nanowire 104 determines the width of the nanochannel 108. The diameter of nanochannel 108 can range from nanometers to micrometers, or even larger, which corresponds to the nanowire 104 diameter. Likewise, the length of the nanowire 104 corresponds to the length of the nanochannel 108. The nanowire 104 can be fabricated through standard semiconductor processes or other methods. For a nanowire 104 made of silicon, different diameters of the nanochannel 108 can be obtained by different reactive ion etch or wet etch time. In one case, the carbon nanotube may have a diameter of 1 to 10 nm, and the silicon nanowire may have a diameter up to 100 nm.

In the view B of the top view, the dashed lines show that the newly formed nanochannel 108 runs under the insulating material 105 connecting the opening 106 (e.g., inlet) to the opening 107 (e.g., the outlet). The nanochannel 108 is formed in a desired pattern without having to drill through the insulating material 105 using conventional optical lithography, electron beam lithography, focus ion beam, nanoimprint lithography, and interferometic lithography.

Figure 2A:
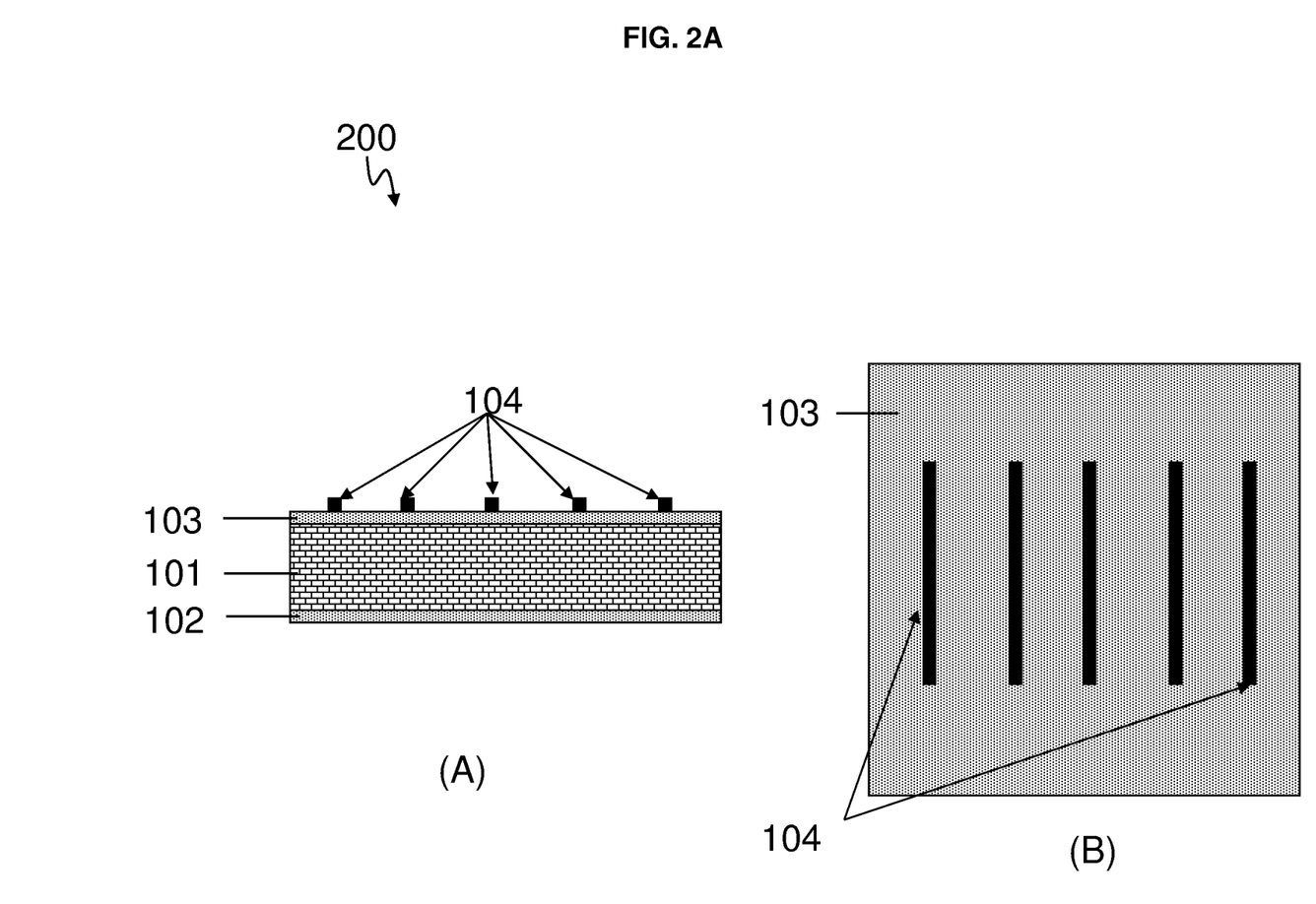
FIG. 2A illustrates an electrically insulating substrate with an electrically insulating thin film underneath and an electrically insulating thin film above, and an array of nanowires are selectively placed on the whole wafer.
Figure 2B:
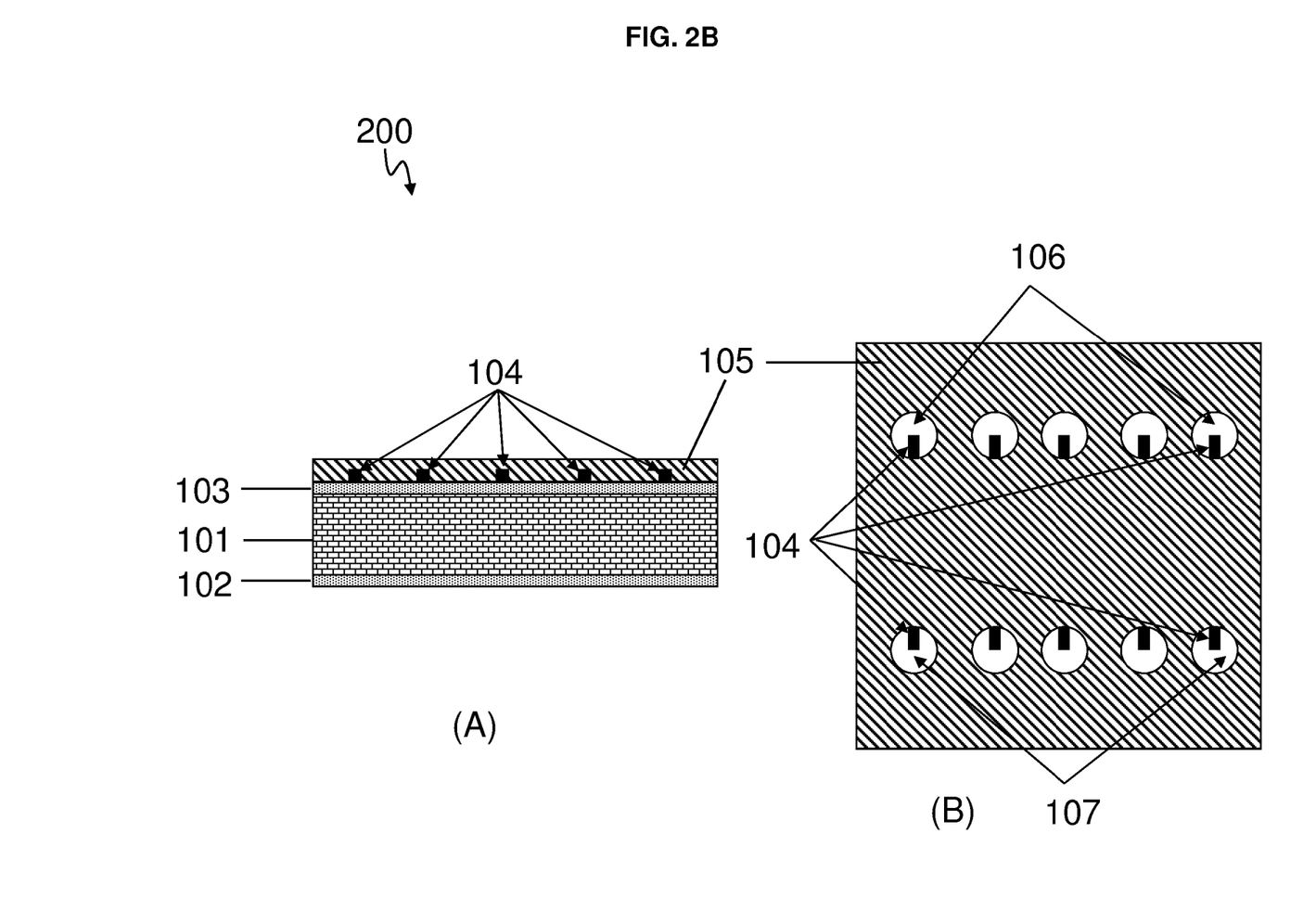
FIG. 2B illustrates the insulating material deposited to cover both the electrically insulating film and the array of the nanowires.
Figure 2C:
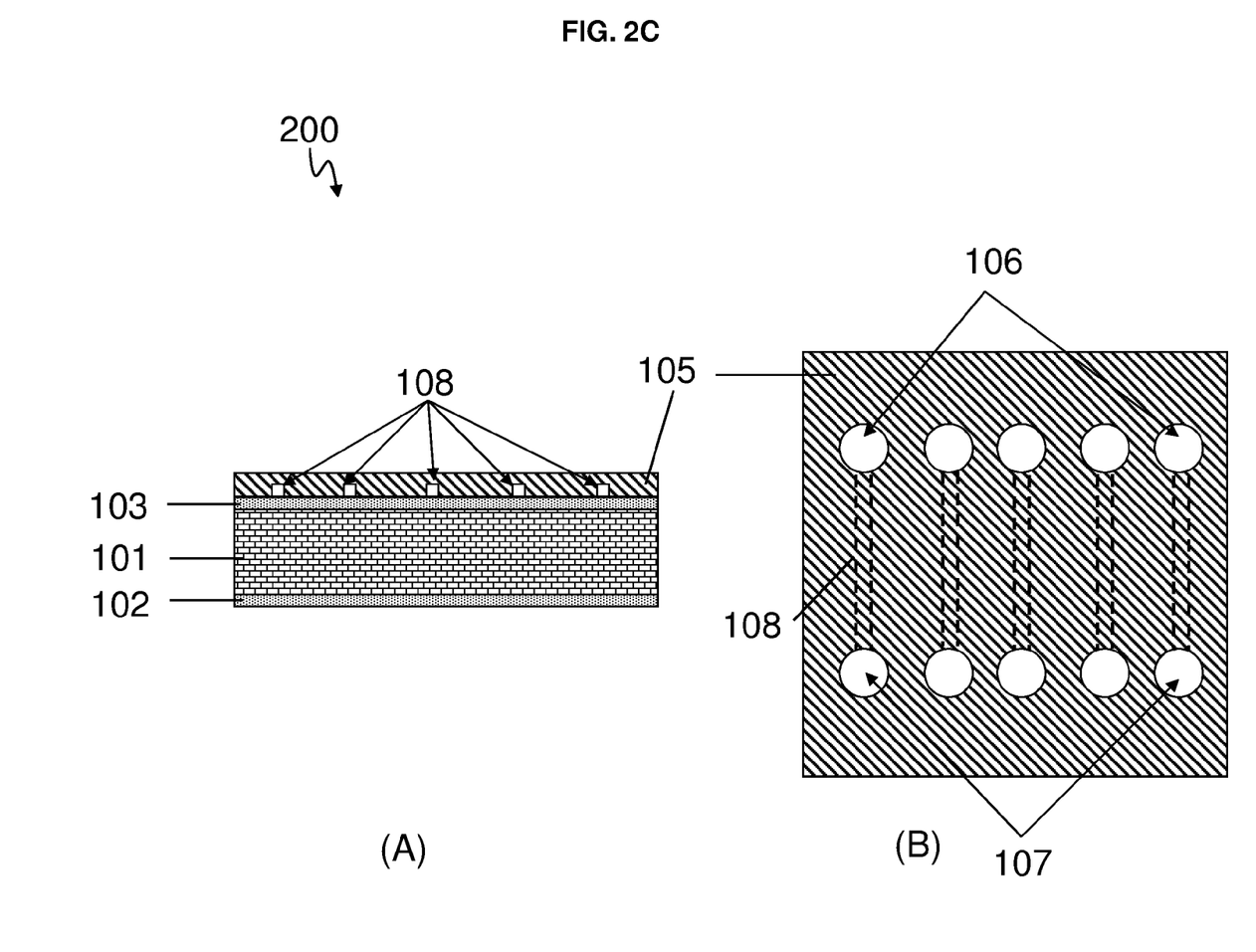
FIG. 2C illustrates the array of nanochannels formed after selectively removing/etching their corresponding nanowires.

FIGS. 2A through 2C illustrate processes to fabricate an array of nanometer channels (i.e., nanochannels 108) at the wafer scale in a nanodevice 200 for DNA/RNA sequencing or peptide detection. The previous discussions of FIGS. 1A through 1D apply to FIGS. 2A through 2C.

FIG. 2A shows the cross-sectional view (A) and the top view (B) of an array of nanometer wires, which are nanowires 104. The electrically insulating substrate 101 (which may be silicon) has electrically insulating film 103 deposited on top and electrically insulating film 102 deposited underneath. The array of nanowires 104 are selectively placed on the whole wafer.

In FIG. 2B, the insulating material 105 is deposited to completely cover both the top of the electrically insulating film 103 and the array of nanowires 104. The openings 106 and 107 are created to allow two ends (e.g., first tips and second tips) of an individual nanowire 104 to be exposed.

In FIG. 2C, each of the nanochannels (nanometer channels) 108 is formed after selectively removing (i.e., etching away) their corresponding nanowires 104. The openings 106 and 107 are utilized as the inlets and outlets of a fluidic nanochannel 108, as well as the openings for the previous etching. Each nanochannel 108 is individually accessed through its respective inlet and outlet (i.e., opening 106 and 107). The dashed lines show that the array of nanochannels 108 runs underneath the electrically insulating material 105 connecting the respective openings 106 to the openings 107. In one case, nanowires 104 with different diameters (e.g., carbon nanotubes with different diameters) may be utilized to make corresponding nanochannels 108 with different diameters.

Figure 3A:
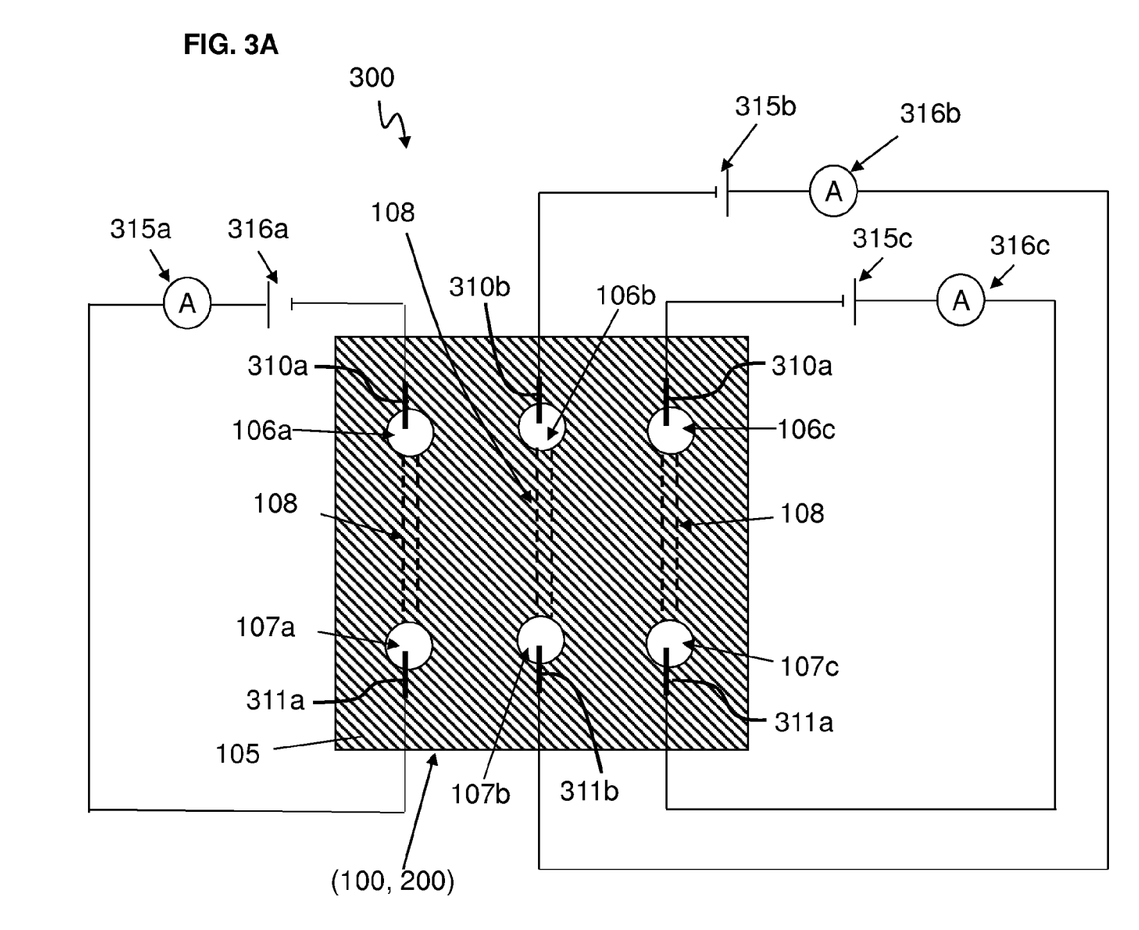
FIG. 3A is a top view of a system for sequencing and/or detection in the nanodevice according to an embodiment.
Figure 3B:
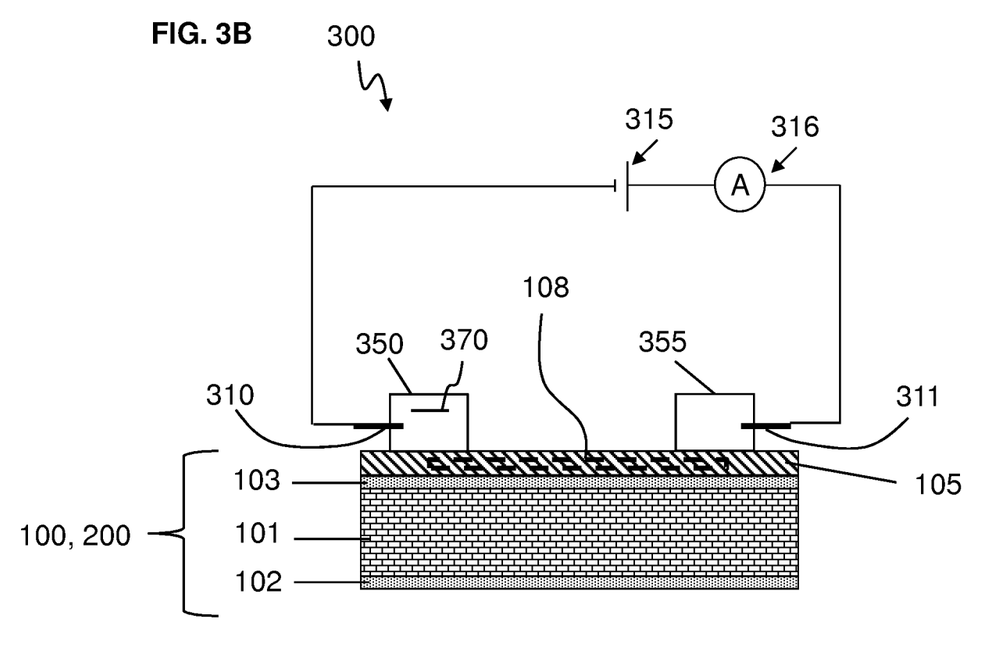
FIG. 3B is a side view of the system according to an embodiment.

FIGS. 3A and 3B illustrate a system 300 for DNA/RNA sequencing or peptide detection in the nanodevice 100, 200. FIG. 3A shows a top view and FIG. 3B shows a side view of the system 300. For the sake of brevity, the system 300 only shows 3 nanochannels 108 but it is understood that more or less than 3 nanochannels 108 may be included as desired. The nanodevice 100, 200 includes all the layers as discussed herein, and discussion of the various layers is not repeated.

The openings 106 are particularly identified as (inlet) openings 106a, 106b, and 106c, which are respectively connected to its own reservoir 350 (shown in FIG. 3B). The openings 107 are particularly identified as (outlet) openings 107a, 107b, and 107c, which are respectively connected to its own reservoir 355. Although not shown in FIG. 3A, an individual reservoir 350 is sealed to and positioned on top of respective openings 106a, 106b, and 106c. Similarly, an individual reservoir 355 is sealed to and positioned on top of respective openings 107a, 107b, and 107c. The respective reservoirs 350 and 355 have been lifted off in the top view.

An electrode 310a, 310b, and 310c is respectively in its own individual reservoir 350 that is positioned over a corresponding opening 106a, 106b, and 106c. Similarly, an electrode 311a, 311b, and 311c is respectively in its own individual reservoir 355 that is positioned over a corresponding opening 107a, 107b, and 107c.

Accordingly, a corresponding nanochannel 108 is connected to its own inlet reservoir 350 via its inlet opening 106 and is connected to its own outlet reservoir 355 via its opening 107. Each reservoir 350, each nanochannel 108, and each reservoir 355 are all filled with an electrically conductive solution. The electrically conductive solution may be an electrolyte solution as understood by one skilled in the art.

The samples of DNA or peptide (represented as molecule(s) 370) can be introduced (e.g., by a syringe or pump) into the respective reservoir 350 for sequencing using one of the known techniques when the DNA molecule 370 is the nanochannel 108. The electrodes 310a, 310b, and 310c and electrodes 311a, 311b, and 311c may be Ag/AgCl electrodes, which can provide the electrical field inside respective nanochannels 108 via voltage from respective voltage sources 316a, 316b, and 316c. The individual current in each respective nanochannel 108 can be monitored through respective current meters 315a, 315b, and 315c, and the bases of the DNA molecule 370 can be read as understood by one skilled in the art.

Figure 4A:
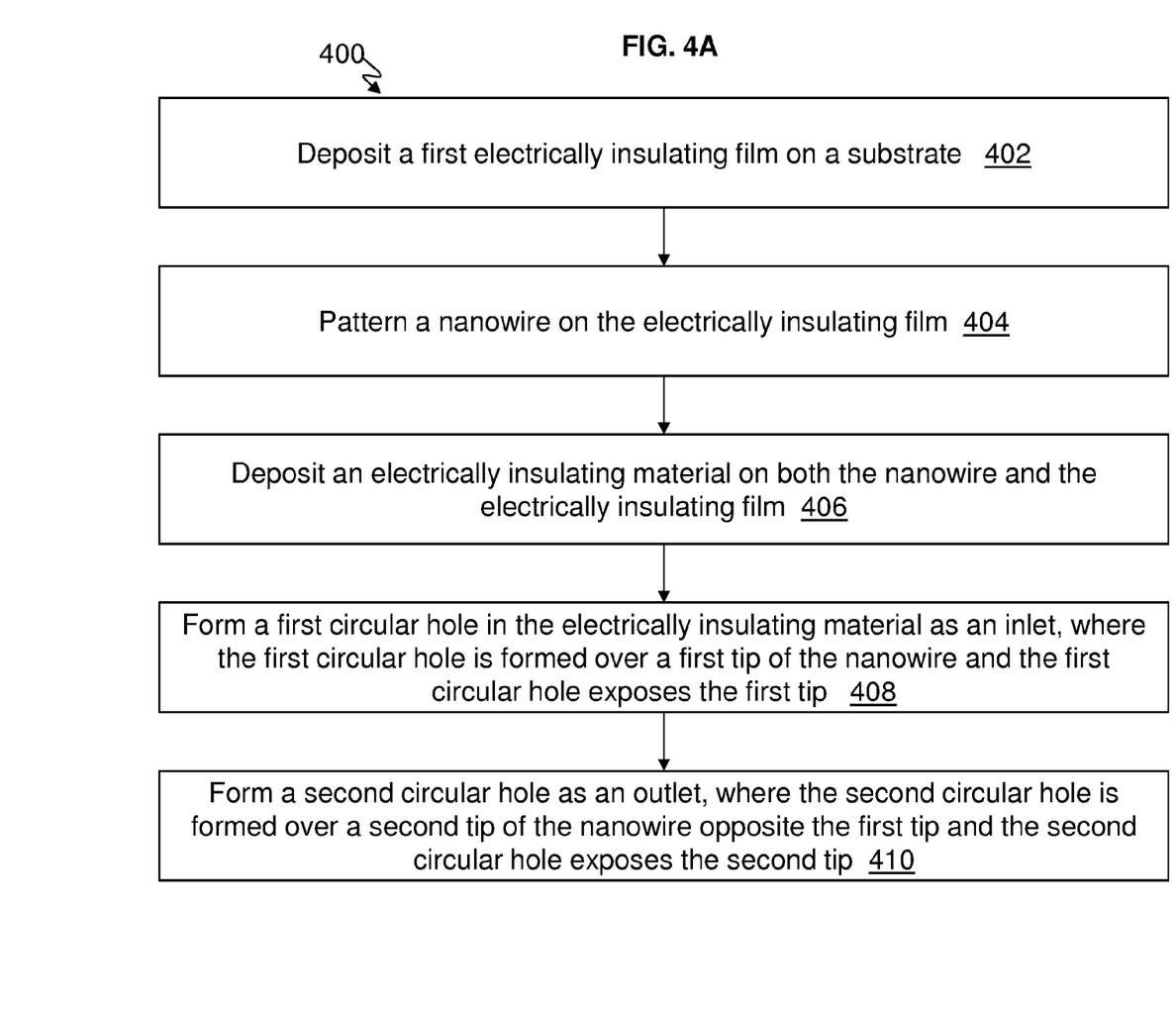
FIGS. 4A and 4B together illustrate a method of fabricating nanochannels for the nanodevice according to an embodiment.
Figure 4B:
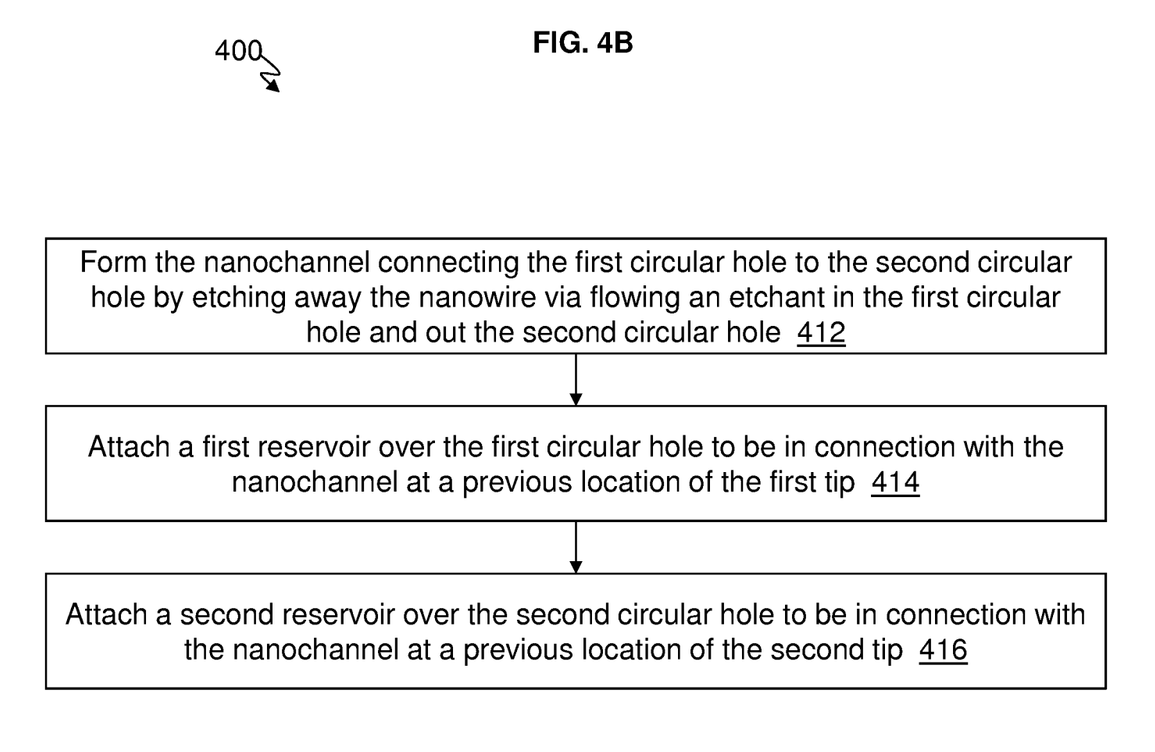

FIGS. 4A and 4B illustrate a method 400 for fabricating nanochannels 108 for the nanodevice 100, 200 according to an embodiment. Reference can be made to FIGS. 1, 2, 3, and 5 in any combination.

The electrically insulating film 103 is deposited on the substrate 101 at block 402. The nanowire(s) 104 are patterned on the electrically insulating film 103 at block 404. The electrically insulating material 105 is deposited on and covers both the nanowires 104 and the electrically insulating film 103 at block 406.

The first circular holes/openings 106 are respectively formed in the electrically insulating material 105 as inlets, where the first circular holes/openings 106 are formed over the first tips (shown in FIGS. 1C and 2B) of the nanowires 104 and the first circular holes/openings 106 expose the first tips at block 408. The length of the exposed first tip of the nanowire 104 in the opening 106 may be few (e.g., 1, 2, 3, 4, 5 . . . 9) or tens (e.g., 10, 15, 20, 25, etc.) of nanometers.

At block 410, the second circular holes/openings are respectively formed in the electrically insulating material 105 as outlets, where the second circular holes/openings 107 are formed over second tips of the nanowires 104 opposite the first tips and the second circular holes/openings 107 expose the second tips. The length of the exposed second tips of the nanowire 104 in the opening 107 may be few (e.g., 1, 2, 3, 4, 5 . . . 9) or tens (e.g., 10, 15, 20, 25, etc.) of nanometers.

The nanochannels 108 respectively connecting the first circular holes/openings 106 to the second circular holes/openings 107 are formed by etching away the nanowires 104 via flowing an etchant in the first circular holes/openings 106 and out the second circular holes/openings 107 at block 412.

The first reservoir 350 is attached (and sealed) over the first circular holes/openings 106 (as shown in FIG. 3B) to be in connection with the respective nanochannel 108 at the previous location of first tip at block 414.

The second reservoir 355 is attached (and sealed) over the second circular holes/openings 107 to be in connection with the respective nanochannels at the previous location of the second tip at block 416.

The nanochannels 108 are self-formed by removing the respective nanowires 104. The first reservoirs 350, the second reservoirs 355, and the nanochannels 108 are all filled with an electrically conductive solution.

The method utilizes the first circular holes/openings 106 as both the inlets for flowing the etchant to originally form the respective nanochannels 108 and as the inlets for driving (via voltage of the voltage source 315) molecule(s) 370 from the respective first reservoirs 350 into their respectively connected nanochannels 108. The method includes utilizing the second circular holes/openings 107 as both the outlets for exiting the etchant to originally form the respective nanochannels 108 and as the outlets for driving the molecule from the nanochannels 108 into the second reservoirs 355.

In FIGS. 3A and 3B, the voltage source 315 generates an electric field that drives the molecule 370 from the first reservoir 350, through the first circular hole/opening 106, into the nanochannel 108, through the second circular hole 107, and out into the second reservoir 355. The system 300 sequences the molecule 370 while in the nanochannel 108.

The first circular hole/opening 106 is a first connection from the first reservoir 350 to the nanochannel 108, and the second circular hole/openings 107 is a second connection from the second reservoir 355 to the nanochannel 108.

The nanowires 104 may be a carbon nanotube, where the etchant removes the respective carbon nanotubes to leave behind the nanochannels 108 without affecting the insulating material 105. The diameter of the nanochannels 108 is caused by and corresponds to the diameter of the respective carbon nanotubes. Also, the length of the nanochannels 108 is caused by and corresponds to the length of the carbon nanotubes.

The depth of the first circular holes/openings 106 is down to the carbon nanotube at the first tip without reaching the substrate 101, and depth of the second circular holes/openings 107 is down to the carbon nanotube at the second tip without reaching the substrate 101.

Figure 5:
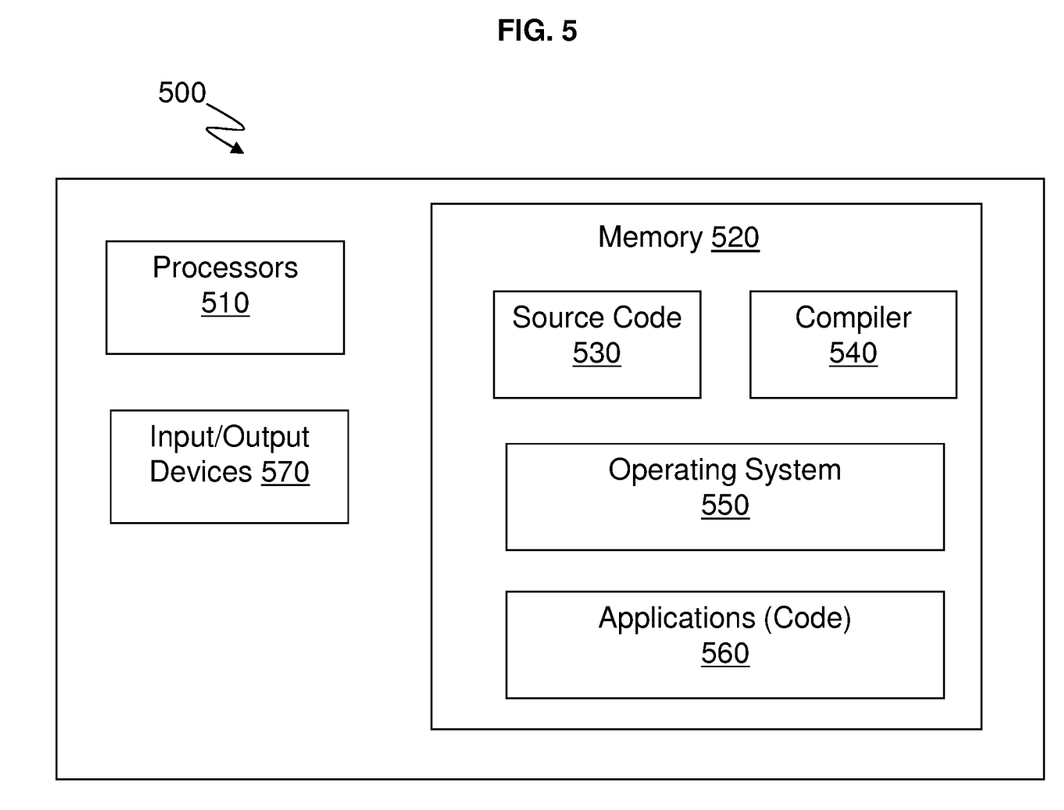
FIG. 5 is a block diagram that illustrates an example of a computer (computer test setup) having capabilities, which may be included in and/or combined with embodiments.

FIG. 5 illustrates an example of a computer 500 (e.g., as part of the computer test setup for testing and analysis) which may implement, control, and/or regulate the voltage source 315, and measurements of the ammeter 316 as discussed herein.

Various methods, procedures, modules, flow diagrams, tools, applications, circuits, elements, and techniques discussed herein may also incorporate and/or utilize the capabilities of the computer 500. Moreover, capabilities of the computer 500 may be utilized to implement features of exemplary embodiments discussed herein. One or more of the capabilities of the computer 500 may be utilized to implement, to connect to, and/or to support any element discussed herein (as understood by one skilled in the art) in FIGS. 1-4. For example, the computer 500 which may be any type of computing device and/or test equipment (including ammeters, voltage sources, connectors, etc.). Input/output device 570 (having proper software and hardware) of computer 500 may include and/or be coupled to the nanodevices and structures discussed herein via cables, plugs, wires, electrodes, patch clamps, etc. Also, the communication interface of the input/output devices 570 comprises hardware and software for communicating with, operatively connecting to, reading, and/or controlling voltage sources, ammeters, and current traces (e.g., magnitude and time duration of current), etc., as discussed herein. The user interfaces of the input/output device 570 may include, e.g., a track ball, mouse, pointing device, keyboard, touch screen, etc., for interacting with the computer 500, such as inputting information, making selections, independently controlling different voltages sources, and/or displaying, viewing and recording current traces for each base, molecule, biomolecules, etc.

Generally, in terms of hardware architecture, the computer 500 may include one or more processors 510, computer readable storage memory 520, and one or more input and/or output (I/O) devices 570 that are communicatively coupled via a local interface (not shown). The local interface can be, for example but not limited to, one or more buses or other wired or wireless connections, as is known in the art. The local interface may have additional elements, such as controllers, buffers (caches), drivers, repeaters, and receivers, to enable communications. Further, the local interface may include address, control, and/or data connections to enable appropriate communications among the aforementioned components.

The processor 510 is a hardware device for executing software that can be stored in the memory 520. The processor 510 can be virtually any custom made or commercially available processor, a central processing unit (CPU), a data signal processor (DSP), or an auxiliary processor among several processors associated with the computer 500, and the processor 510 may be a semiconductor based microprocessor (in the form of a microchip) or a macroprocessor.

The computer readable memory 520 can include any one or combination of volatile memory elements (e.g., random access memory (RAM), such as dynamic random access memory (DRAM), static random access memory (SRAM), etc.) and nonvolatile memory elements (e.g., ROM, erasable programmable read only memory (EPROM), electronically erasable programmable read only memory (EEPROM), programmable read only memory (PROM), tape, compact disc read only memory (CD-ROM), disk, diskette, cartridge, cassette or the like, etc.). Moreover, the memory 520 may incorporate electronic, magnetic, optical, and/or other types of storage media. Note that the memory 520 can have a distributed architecture, where various components are situated remote from one another, but can be accessed by the processor 510.

The software in the computer readable memory 520 may include one or more separate programs, each of which comprises an ordered listing of executable instructions for implementing logical functions. The software in the memory 520 includes a suitable operating system (O/S) 550, compiler 540, source code 530, and one or more applications 560 of the exemplary embodiments. As illustrated, the application 560 comprises numerous functional components for implementing the features, processes, methods, functions, and operations of the exemplary embodiments.

The operating system 550 may control the execution of other computer programs, and provides scheduling, input-output control, file and data management, memory management, and communication control and related services.

The application 560 may be a source program, executable program (object code), script, or any other entity comprising a set of instructions to be performed. When a source program, then the program is usually translated via a compiler (such as the compiler 540), assembler, interpreter, or the like, which may or may not be included within the memory 520, so as to operate properly in connection with the O/S 550. Furthermore, the application 560 can be written as (a) an object oriented programming language, which has classes of data and methods, or (b) a procedure programming language, which has routines, subroutines, and/or functions.

The I/O devices 570 may include input devices (or peripherals) such as, for example but not limited to, a mouse, keyboard, scanner, microphone, camera, etc. Furthermore, the I/O devices 570 may also include output devices (or peripherals), for example but not limited to, a printer, display, etc. Finally, the I/O devices 570 may further include devices that communicate both inputs and outputs, for instance but not limited to, a NIC or modulator/demodulator (for accessing remote devices, other files, devices, systems, or a network), a radio frequency (RF) or other transceiver, a telephonic interface, a bridge, a router, etc. The I/O devices 570 also include components for communicating over various networks, such as the Internet or an intranet. The I/O devices 570 may be connected to and/or communicate with the processor 510 utilizing Bluetooth connections and cables (via, e.g., Universal Serial Bus (USB) ports, serial ports, parallel ports, FireWire, HDMI (High-Definition Multimedia Interface), etc.).

In exemplary embodiments, where the application 560 is implemented in hardware, the application 560 can be implemented with any one or a combination of the following technologies, which are each well known in the art: a discrete logic circuit(s) having logic gates for implementing logic functions upon data signals, an application specific integrated circuit (ASIC) having appropriate combinational logic gates, a programmable gate array(s) (PGA), a field programmable gate array (FPGA), etc.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one more other features, integers, steps, operations, element components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated The flow diagrams depicted herein are just one example. There may be many variations to this diagram or the steps (or operations) described therein without departing from the spirit of the invention. For instance, the steps may be performed in a differing order or steps may be added, deleted or modified. All of these variations are considered a part of the claimed invention.

While the preferred embodiment to the invention had been described, it will be understood that those skilled in the art, both now and in the future, may make various improvements and enhancements which fall within the scope of the claims which follow. These claims should be construed to maintain the proper protection for the invention first described.

What is claimed is:

1. A method for fabricating nanochannels for a nanodevice, the method comprising:
   depositing an electrically insulating film on a substrate;
   patterning a nanowire on the electrically insulating film;
   depositing an electrically insulating material on both the nanowire and the electrically insulating film;
   forming a first circular hole in the electrically insulating material as an inlet, the first circular hole formed over a first tip of the nanowire, the first circular hole exposing the first tip;
   forming a second circular hole as an outlet, the second circular hole formed over a second tip of the nanowire opposite the first tip, the second circular hole exposing the second tip;
   forming a nanochannel connecting the first circular hole to the second circular hole by etching away the nanowire via flowing an etchant in the first circular hole and out the second circular hole;
   attaching a first reservoir over the first circular hole to be in connection with the nanochannel at a previous location of the first tip; and
   attaching a second reservoir over the second circular hole to be in connection with the nanochannel at a previous location of the second tip.

2. The method of claim 1, wherein the nanochannel is self-formed by removing the nanowire.

3. The method of claim 1, further comprising filling the first reservoir, the second reservoir, and the nanochannel with an electrically conductive solution.

4. The method of claim 1, further comprising utilizing the first circular hole as both the inlet for flowing the etchant to form the nanochannel and as the inlet for driving a molecule from the first reservoir into the nanochannel.

5. The method of claim 4, further comprising utilizing the second circular hole as both the outlet for exiting the etchant to form the nanochannel and as the outlet for driving the molecule from the nanochannel into the second reservoir.

6. The method of claim 1, wherein the first circular hole is a first connection from the first reservoir to the nanochannel; and
   wherein the second circular hole is a second connection from the second reservoir to the nanochannel.

7. The method of claim 6, further comprising driving a molecule from the first reservoir, through the first circular hole, into the nanochannel, through the second circular hole, and out to the second reservoir.

8. The method of claim 7, further comprising sequencing the molecule while in the nanochannel.

9. The method of claim 1, wherein the nanowire is a carbon nanotube.

10. The method of claim 9, wherein the etchant removes the carbon nanotube to leave the nano channel.

11. The method of claim 10, wherein a diameter of the nanochannel is caused by and corresponds to a diameter of the carbon nanotube.

12. The method of claim 11, wherein a length of the nanochannel is caused by and corresponds to a length of the carbon nanotube.

13. The method of claim 12, wherein a first depth of the first circular hole is down to the carbon nanotube at the first tip without reaching the substrate; and
   wherein a second depth of the second circular hole is down to the carbon nanotube at the second tip without reaching the substrate.

14. A method for fabricating nanochannels for a nanodevice, the method comprising:
   depositing an electrically insulating film on a substrate;
   patterning nanowires on the electrically insulating film;
   depositing an electrically insulating material on both the nanowires and the electrically insulating film;
   forming first circular holes in the electrically insulating material as inlets, the first circular holes respectively formed over first tips of the nanowires, the first circular holes respectively exposing the first tips;
   forming second circular holes as outlets, the second circular holes respectively formed over second tips of the nanowires opposite the first tips, the second circular holes respectively exposing the second tips;
   forming the nanochannels respectively connecting the first circular holes to the second circular holes by etching away the nanowires via flowing an etchant in the first circular holes and out the second circular holes;
   attaching first reservoirs individually over the first circular holes to be in connection respectively with the nanochannels at previous locations of the first tips; and
   attaching second reservoirs individually over the second circular holes to be in connection respectively with the nanochannels at previous locations of the second tips.

15. The method of claim 14, wherein the nanochannels are self-formed by removing the nanowires.

16. The method of claim 14, further comprising filling the first reservoirs, the second reservoirs, and the nanochannels with an electrically conductive solution.

17. The method of claim 14, further comprising utilizing the first circular holes as both the inlets for flowing the etchant to respectively form the nanochannels and as the inlets for driving a molecule from the first reservoirs into the nanochannels.

18. The method of claim 17, further comprising utilizing the second circular holes as both the outlets for exiting the etchant to respectively form the nanochannels and as the outlets for driving the molecule from the nanochannels into the second reservoirs.

19. The method of claim 14, wherein the first circular holes are a first connection from the first reservoirs to the nanochannels; and
   wherein the second circular holes are a second connection from the second reservoirs to the nanochannels.

20. The method of claim 14, wherein the nanochannels are carbon nanotubes.

* * * * *